United States Patent [19]

Cumberland

[11] Patent Number: 4,805,603
[45] Date of Patent: Feb. 21, 1989

[54] INFLATABLE CERVICAL TRACTION PILLOW

[76] Inventor: Keith Cumberland, 1314 Concerde Ave., Amory, Monroe County, Miss. 38821

[21] Appl. No.: 218,163

[22] Filed: Jul. 13, 1988

[51] Int. Cl.$^4$ .............................. A47G 9/00; A61F 5/00
[52] U.S. Cl. .......................................... 128/75; 5/436; 5/441; 128/DIG. 20
[58] Field of Search ................... 5/441, 434, 436, 442; 128/71, 75, 76 R, DIG. 20

[56] References Cited

U.S. PATENT DOCUMENTS 3,411,164 11/1968 Sumergrade ............................. 5/441
3,753,264 8/1973 Grenier ................................... 5/436
4,501,034 2/1985 Greenwalt .............................. 5/441

FOREIGN PATENT DOCUMENTS 1120734 7/1956 France .................................... 5/441

Primary Examiner—Alexander Grosz

[57] ABSTRACT

A cervical traction apparatus comprising a head/neck/shoulder support unit having a vertical slot in the region corresponding to the cervical area, said slot separating said unit into a first section and a second section, the upper surfaces of said support unit being shaped to receive the head, neck and shoulders of a reclining person, an inflatable air sac located within said unit between said first and second sections and means for inflating said air sac so as to cause said first and second sections to separate.

6 Claims, 3 Drawing Sheets

INFLATABLE CERVICAL TRACTION PILLOW

This invention relates to an apparatus for applying intermittent or cervical traction.

BACKGROUND OF THE INVENTION

Present-day home cervical traction devices involve complicated and/or cumbersome equipment of numerous parts such as the over-the-door units that often require the attachment of weights and the like. Such devices have been criticized generally for their lack of comfort, and specifically for the stress they cause on the lower back as well as the neck and shoulders, particularly during set-up. In addition, these prior art traction devices are frequently difficult to set-up and manage.

Pillows of various types for supporting the neck and head of a supine person are also known. U.S. Pat. No. 4,528,705 to Monte H. Greenawalt describes a composite pear-shaped pillow having a cavity within which is placed an inflatable air bag. Similarly, U.S. Pat. No. 4,501,034 to Monte H. Greenawalt describes an inflatable pillow for receiving the neck or cervical region of a person wherein the pillow is provided with two separate cavities containing inflatable bags. In both instances, however, the pillows simply provide support for the user's neck and head at a desired degree of firmness and are incapable of effecting any cervical traction.

It is an object of the invention to provide a cervical traction apparatus that can be used to help relieve muscle tension and spasm, neck pain, headaches and the like.

It is also an object of the invention to provide a cervical traction apparatus of minimum parts that is easy to set-up and use.

Another object of the invention is to provide a cervical traction device that offers a greater comfort factor than the prior art traction devices.

Yet another object of the invention is to provide a cervical traction apparatus whose pull is limited to cervical neck region, thereby eliminating pull on the jaw, TMJ joint and other parts of the body.

A further object of the invention is to provide a cervical traction apparatus that enables the patient to lie down and rest when the apparatus is in use.

Another object of the invention is a cervical traction device that can also be used as a pillow for a more restful sleep.

SUMMARY OF THE INVENTION

These and other objects of the invention are provided by a cervical traction apparatus comprising a head/neck/shoulder support unit having a vertical slot in the region corresponding to the cervical area, said slot separating said unit into a first section and a second section, the upper surfaces of said support unit being shaped to receive the head, neck and shoulders of a reclining person, an inflatable air sac located within said unit between said first and second sections and means for inflating said air sac so as to cause said first and second sections to separate.

DETAILED DESCRIPTION OF A PREFERRED EMBODIMENT

Figure 1:
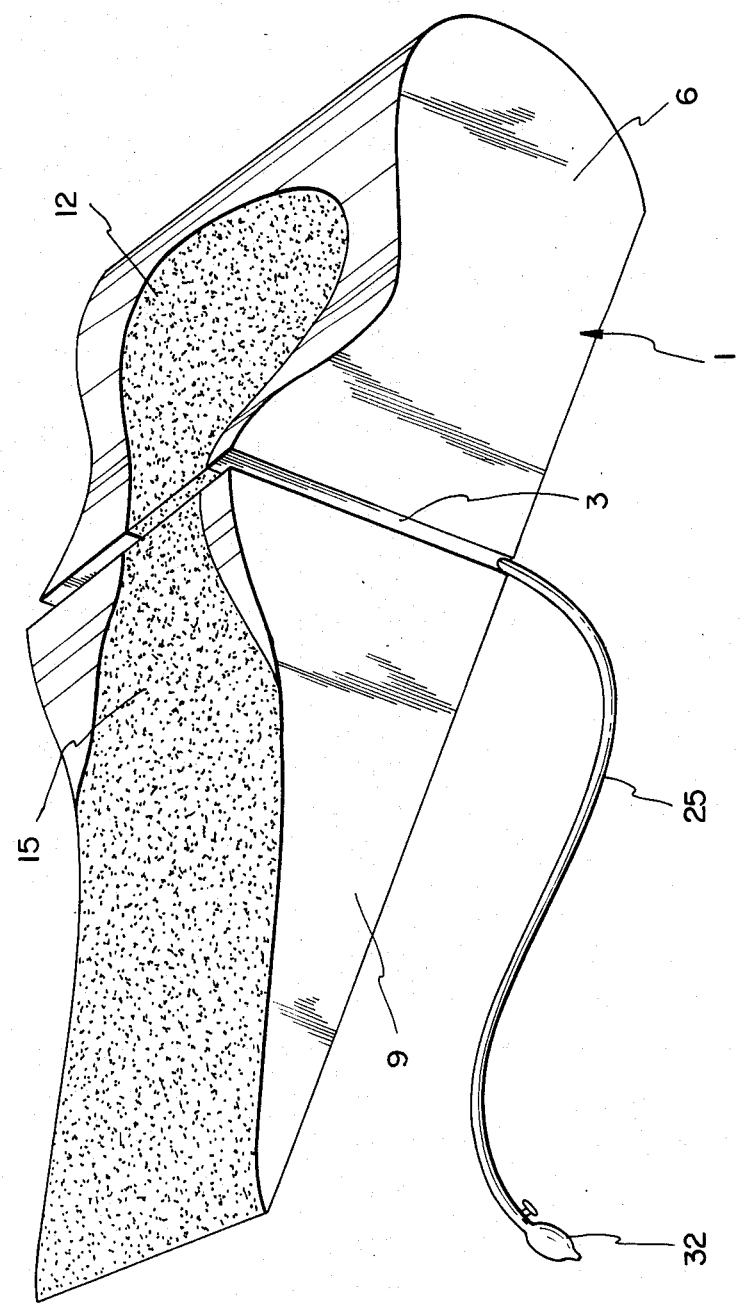
FIG. 1 is a perspective view of the cervical traction apparatus of the invention.

The cervical traction apparatus of the invention comprises a head/neck/shoulder support unit designated in its entirety as 1 and containing a vertical slot 3 that separates the unit into two adjoining sections 6 and 9. The upper surfaces of sections 6 and 9 are shaped to conform to and receive the head, neck and shoulders of the reclining person (see FIG. 3). The head will be positioned on surface area 12 of section 6 and the shoulders on surface area 15 of section 9. As can be seen from the figures, section 9 is preferably elongated to stabilize the support unit during use. Each section 6 and 9 can be constructed of a comfortable resilient material such as foamed synthetic or natural rubber or it can be fabricated in the form of a more traditional pillow.

Figure 2:
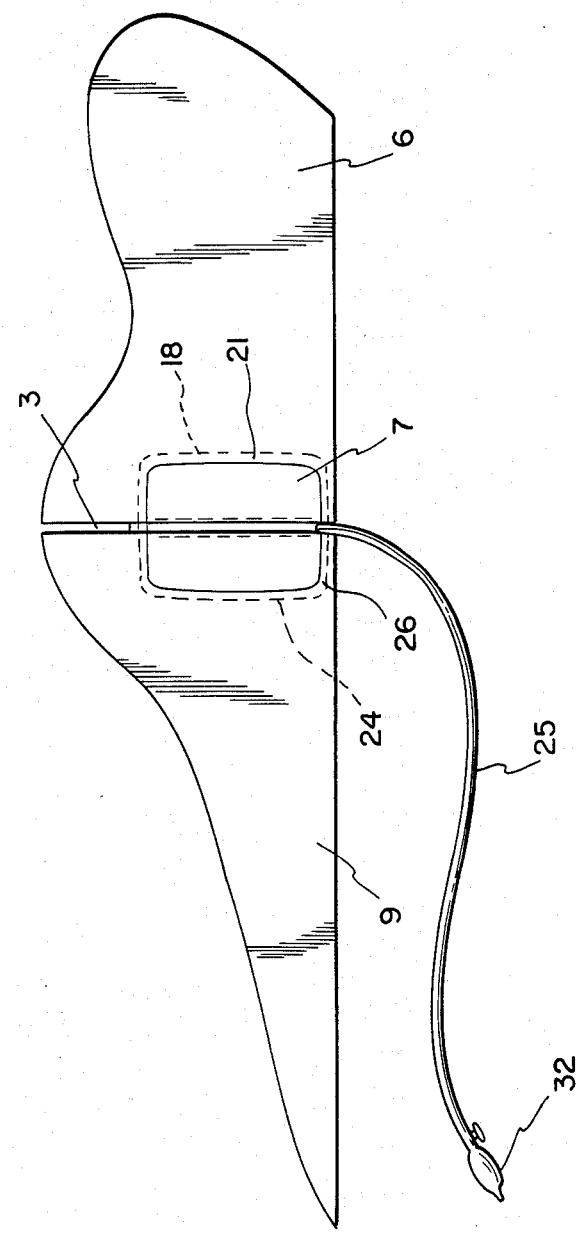
FIG. 2 is a side cross-section of the invention showing the location of the air sac within the support unit in non-inflated condition.

Referring to FIG. 2, a support unit 1 contains a compartment, indicated generally as 18, made up of two halves 21 and 24 which face each other and are separated by slot 3. Half 21 is located in section 6 and half 24 is located in section 9. Cavity 18 accommodates an inflatable air sac or bladder 26. The size and shape of cavity 18 may vary depending principally on the size and shape of the air sac employed. However, it is important that the air sac 26 be inflatable to a cross-sectional area that exceeds the cross-sectional area of cavity 18 so that on inflation the sac 26 eventually expands to further separate part 6 from part 9. Thus, the air sac can be constructed from any expandable material such as rubber or other elastomeric material.

An inflating tube 25 contains a hand pump 32 of the releasable check valve type at one end and communicates at its other end with air sac 26. Hand pump 32 with its check valve enables the user himself, to inflate and deflate the air sac at will while lying down. Advantageously, tube 29 is long enough for the patient to reach without strain.

Figure 3:
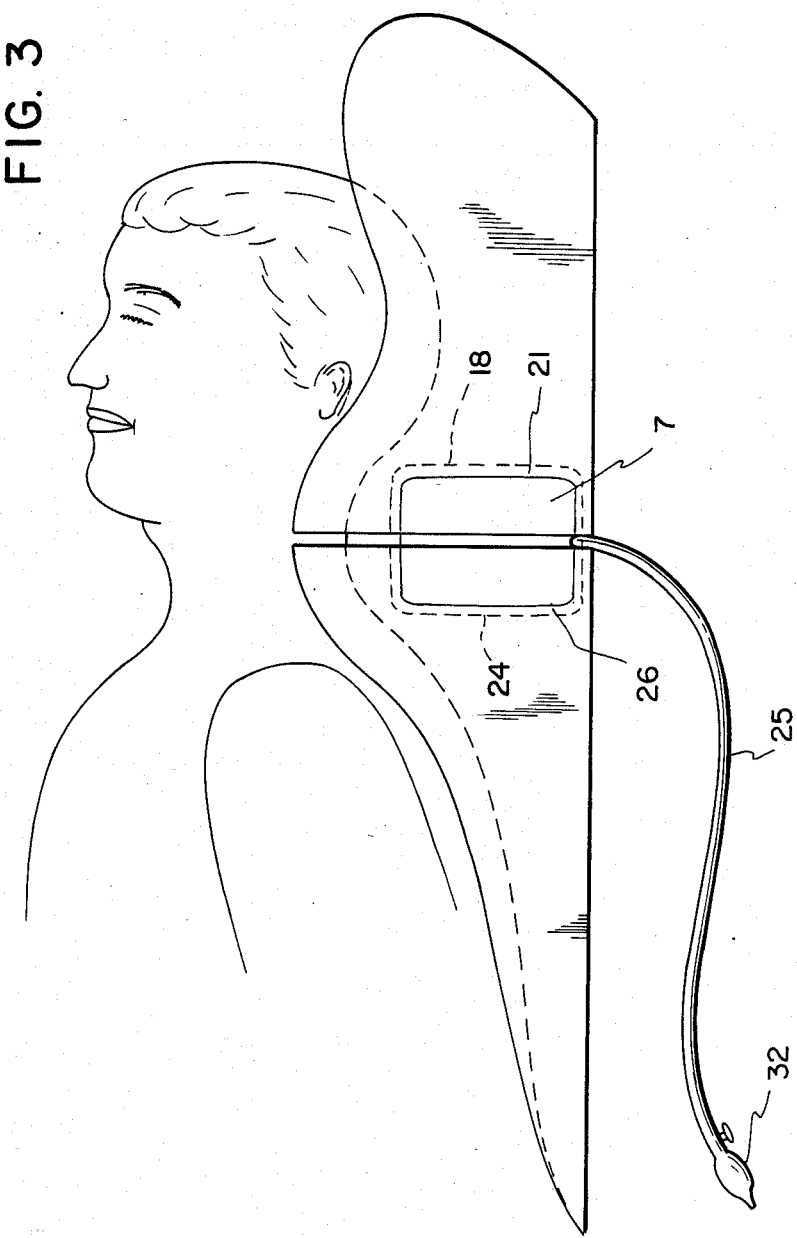
FIG. 3 is a side view of the cervical traction apparatus of the invention in operation with the air sac in inflated condition.

Referring to FIG. 3, a patient is treated in a supine position with the slot 3 positioned at the cervical area of the patient, the head positioned on section 6 and the shoulders supported on section 9. Using hand pump 32, air sac 26 is inflated until expansion of sac 26 separates sections 6 and 9. However, when the patient is lying on the support unit, section 9 is stabilized by the upper back and only section 6 moves to increase the width of slot 3 as show in FIG. 3 thereby providing the desired traction. The release of the air from the air sac will provide an intermittent treatment protocol or a static treatment. Thus, any desired degree of cervical traction can be induced by simply adjusting the amount of air pressure in air sac 26 by incrementally inflating or deflating the sac.

While the features of this invention have been disclosed with reference to the specific embodiment described therein, it is understood that various modifications may be made in the construction without departing from the scope of the invention as defined in the appended claims.

It is claimed:

1. A cervical traction apparatus comprising a head/neck/shoulder support unit having a vertical slot in the region corresponding to the cervical area, said slot separating said unit into a first section and a second section, the upper surfaces of said support unit being shaped to receive the head, neck and shoulders of a reclining person, an inflatable air sac located within said unit between said first and second sections and means for inflating said air sac so as to cause said first and second sections to separate.

2. A cervical traction apparatus according to claim 1 wherein said means for inflating said air sac comprises a conduit communicating with said air sac and an air pump connected to said conduit.

3. A cervical traction apparatus according to claim 2 wherein said conduit and said air pump extend exteriorly of said unit.

4. A cervical traction apparatus according to claim 3 wherein the air pump is a hand pump of the releasable check valve type.

5. A cervical traction apparatus according to claim 1 including a compartment within said support unit between said first and second sections in which an inflatable sac is disposed.

6. A cervical traction apparatus according to claim 5 wherein the said compartment comprises two halves, one half being located in said first section and the other half being located in said second section, said halves being separated by said slot.

* * * * *